US011053395B2

(12) United States Patent
Karles et al.

(10) Patent No.: US 11,053,395 B2
(45) Date of Patent: Jul. 6, 2021

(54) CORROSION-RESISTANT RESERVOIR FOR AN E-VAPING DEVICE AND METHOD OF MANUFACTURING THEREOF

(71) Applicant: Altria Client Services LLC, Richmond, VA (US)

(72) Inventors: Georgios D. Karles, Richmond, VA (US); Rangaraj S. Sundar, Richmond, VA (US)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 90 days.

(21) Appl. No.: 15/619,997

(22) Filed: Jun. 12, 2017

(65) Prior Publication Data

US 2018/0352857 A1    Dec. 13, 2018

(51) Int. Cl.
*C09D 5/08* (2006.01)
*A61M 11/04* (2006.01)
(Continued)

(52) U.S. Cl.
CPC ............... *C09D 5/08* (2013.01); *A24F 40/70* (2020.01); *A61M 11/042* (2014.02); *A61M 15/06* (2013.01); *C09D 5/44* (2013.01); *C25D 13/06* (2013.01); *A24F 40/10* (2020.01); *A24F 40/42* (2020.01); *A61M 2016/0021* (2013.01); *A61M 2016/0027* (2013.01); *A61M 2205/0238* (2013.01); *A61M 2205/3653* (2013.01); *A61M 2205/8206* (2013.01); *A61M 2205/8237* (2013.01); *B05D 1/02* (2013.01);
(Continued)

(58) Field of Classification Search
CPC ... A24F 47/008; A61M 11/042; A61M 15/06; A61M 15/0091
USPC ............................................. 427/248.1–255.7
See application file for complete search history.

(56) References Cited

U.S. PATENT DOCUMENTS

| 5,591,368 A | 1/1997 | Fleischhauer et al. | |
| 8,997,753 B2 * | 4/2015 | Li | H05B 3/42 |
| | | | 131/273 |

(Continued)

FOREIGN PATENT DOCUMENTS

| CN | 102206848 A | 10/2011 |
| CN | 104249051 A | 12/2014 |

(Continued)

OTHER PUBLICATIONS

Cationic Polymerization (https://polymerdatabase.com/polymer%20chemistry/cationic%20polymerization.html) (Year: 2018).*

(Continued)

*Primary Examiner* — Michael P Wieczorek
*Assistant Examiner* — Michael G Miller
(74) *Attorney, Agent, or Firm* — Harness, Dickey & Pierce, P.L.C.

(57) ABSTRACT

Example embodiments relate to a method of protecting a surface of an e-vaping device portion from corrosion, the method including preparing a coating mixture configured to protect the surface from corrosion, and coating the surface with a protective coating based on the coating mixture, wherein the coating is performed via one of electrodeposition, dipping, spraying, and vapor deposition, and the coating mixture includes at least one of a silane and a resin.

32 Claims, 6 Drawing Sheets

(51) Int. Cl.
| | |
|---|---|
| *A61M 15/06* | (2006.01) |
| *C09D 5/44* | (2006.01) |
| *C25D 13/06* | (2006.01) |
| *A24F 40/70* | (2020.01) |
| *B05D 1/00* | (2006.01) |
| *B05D 1/02* | (2006.01) |
| *B05D 7/22* | (2006.01) |
| *B05D 7/14* | (2006.01) |
| *B05D 1/18* | (2006.01) |
| *A61M 16/00* | (2006.01) |
| *B05D 3/02* | (2006.01) |
| *A24F 40/10* | (2020.01) |
| *A24F 40/42* | (2020.01) |

(52) U.S. Cl.
CPC ............ *B05D 1/18* (2013.01); *B05D 1/60* (2013.01); *B05D 3/0254* (2013.01); *B05D 7/146* (2013.01); *B05D 7/222* (2013.01); *B05D 2518/10* (2013.01)

(56) References Cited

U.S. PATENT DOCUMENTS

| | | | |
|---|---|---|---|
| 2003/0019493 | A1 | 1/2003 | Narayan et al. |
| 2005/0000531 | A1 | 1/2005 | Shi |
| 2005/0172976 | A1 | 8/2005 | Newman et al. |
| 2007/0035055 | A1 | 2/2007 | Gee et al. |
| 2007/0215168 | A1 | 9/2007 | Banerjee et al. |
| 2011/0049437 | A1 | 3/2011 | Crain et al. |
| 2012/0273589 | A1 | 11/2012 | Hon |
| 2014/0000638 | A1 | 1/2014 | Sebastian et al. |
| 2014/0096782 | A1 | 4/2014 | Ampolini et al. |
| 2014/0102464 | A1 | 4/2014 | von Borstel et al. |
| 2014/0190496 | A1 | 7/2014 | Wensley et al. |
| 2014/0224244 | A1 | 8/2014 | Liu |
| 2014/0261486 | A1 | 9/2014 | Potter et al. |
| 2014/0261495 | A1 | 9/2014 | Novak, III et al. |
| 2015/0184304 | A1 | 7/2015 | Kumar et al. |
| 2015/0201674 | A1 | 7/2015 | Dooly et al. |
| 2015/0216237 | A1 | 8/2015 | Wensley et al. |
| 2015/0257447 | A1* | 9/2015 | Sullivan ............... A24F 47/008 131/329 |
| 2017/0060554 | A1 | 3/2017 | Asami |

FOREIGN PATENT DOCUMENTS

| | | | |
|---|---|---|---|
| CN | 205514212 U | 8/2016 | |
| CN | 106072775 A | 11/2016 | |
| CO | 4340552 A1 | 7/1996 | |
| DE | 1019658 B | 11/1957 | |
| WO | WO-2009059798 A2 * | 5/2009 | ............ C09D 4/00 |
| WO | WO-2011/050964 A1 | 5/2011 | |
| WO | WO-2015035547 A1 | 3/2015 | |
| WO | WO-2015/193456 A1 | 12/2015 | |

OTHER PUBLICATIONS

Hu ("Electrodeposition of silane films on aluminum alloys for corrosion protection", Hu et al, Progress in Organic Coatings 58 (2007) 265-271) (Year: 2007).*

Garcia-Lecina ("Influence of deposition conditions on the protective behavior of tetraethyl orthosilicate sol-gel films on AA5754 aluminum alloy". Garcia-Lecina et al, Progress in Organic Coatings 74 (2012) 281-287), (Year: 2012).*

Heydarian ("Electrophoretic Deposition Behavior of Chitosan Biopolymer as a Function of Solvent Type", Heydarian et al, Polymer-Plastics Technology and Engineering 54:11, 1193-1200 (2015)) (Year: 2015).*

Mondal ("Protection and Functionalizing of Stainless Steel Surface by Graphene Oxide-Polypyrrole Composite Coating", Mondal et al, J. Chem. Chem. Eng., 8 (2014) 786-793) (Year: 2014).*

International Preliminary Report on Patentability for corresponding Application No. PCT/EP2018/065544, dated Aug. 5, 2019.

Ji et al: "Improving the corrosion performance of epoxy coatings by chemical modification with silane monomers", Surface and Coatings Techno, Elsevier BV, Amsterdam, NL, vol. 201, No. 8, Dec. 13, 2006, pp. 4789-4795, XP005802168, ISSN: 0257-8972, DOI: 10.1016/J.SURFCOAT.2006.09.100.

Girdhari Kumar et al: "Development and Characterization of Corrosion Resistant Coatings Using the Natural Biopolymer Chitosan", ECS Transactions, vol. 1, Jan. 1, 2006, pp. 101-117, XP055585168, DOI: 10.1149/1.2215582.

International Search Report and Written Opinion for International Application No. PCT/EP2018/065544 dated Sep. 27, 2018.

* cited by examiner

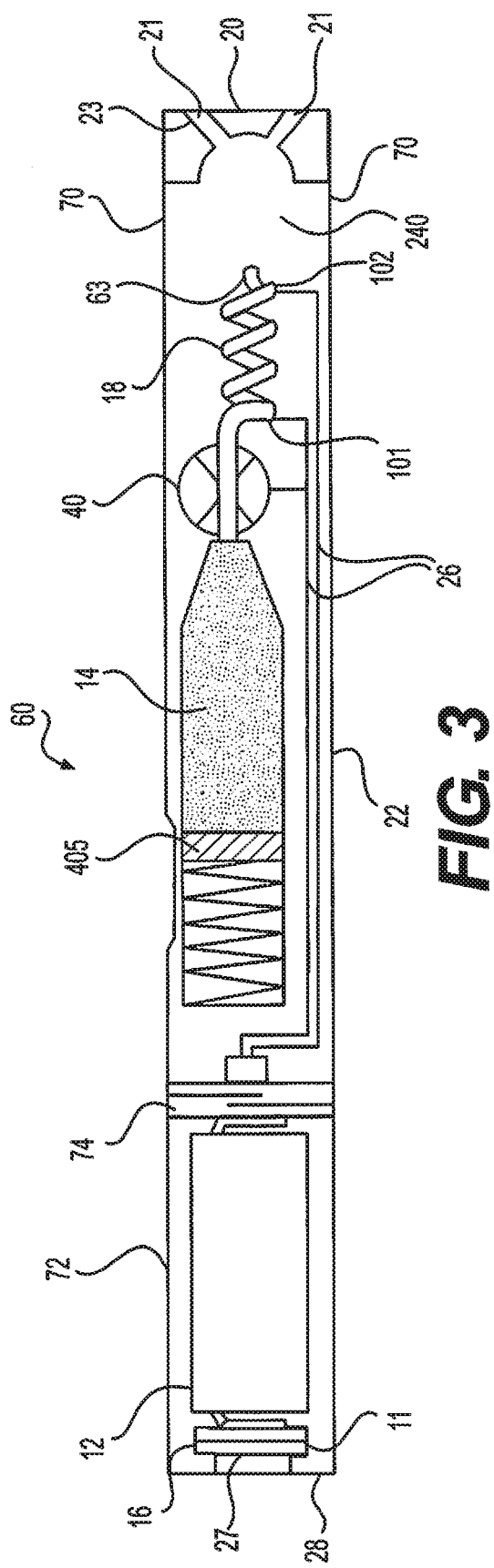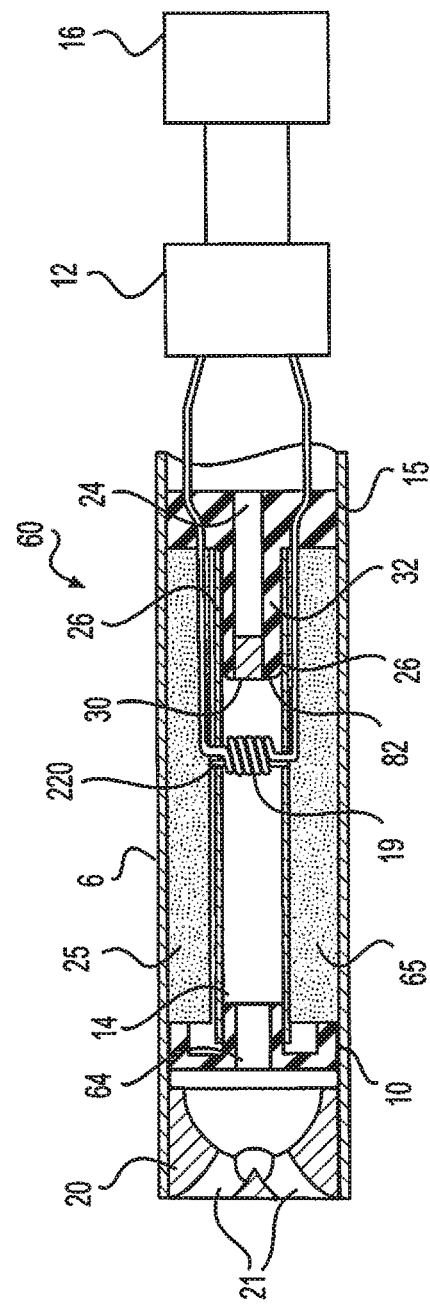

CORROSION-RESISTANT RESERVOIR FOR AN E-VAPING DEVICE AND METHOD OF MANUFACTURING THEREOF

BACKGROUND OF THE INVENTION

Field of the Invention

Example embodiments relate generally to a corrosion-resistant reservoir for an e-vaping device, and/or to a method of manufacturing a corrosion-resistant reservoir for an e-vaping device.

Related Art

Electronic vaping devices are used to vaporize a pre-vapor formulation into a vapor in order for an operator of the e-vaping device to draw the vapor through outlet(s) of the e-vaping device. These electronic vaping devices may be referred to as e-vaping devices. An e-vaping device may typically include several e-vaping elements such as a power supply section and a cartridge. The power supply section includes a power source such as a battery, and the cartridge includes a heater along with a reservoir capable of holding the pre-vapor formulation, the cartridge including a conduit such as a chimney that conveys the vapor to the mouth of the operator of the e-vaping device. The heater in the cartridge is in contact with the pre-vapor formulation via a wick, and is configured to heat the pre-vapor formulation to generate a vapor. The heater may be intertwined with the wick. The pre-vapor formulation typically includes an amount of nicotine and optionally other ingredients such as acids, propylene glycol, glycerol or flavorants. For example, the pre-vapor formulation may include a liquid, solid and/or gel formulation including, but not limited to, water, beads, solvents, active ingredients, ethanol, plant extracts, natural or artificial flavors, and/or vapor formers such as glycerin and/or propylene glycol.

In e-vaping devices, the pre-vaporization formulation included in the reservoir may interact with the metallic portions of the e-vaping device, possibly resulting in the corrosion of the metallic portions, which may lead to a decrease in the stability of the pre-vaporization formulation.

In some instances, ingredients of the pre-vapor formulation may react with solid metallic parts or metal ions of the cartridge. For example, either during operation of the e-vaping device, when the wick of the e-vaping device is not sufficiently supplied with pre-vapor formulation prior to operation of the device by the adult vaper, when the cartridge is empty, or when a coil of the heater is overheating during operation of the e-vaping device, ingredients of the pre-vapor formulation may react with the metal(s) of the solid portions of the e-vaping device, such as copper, brass, steel such as stainless steel or iron, in the presence of oxygen and cause corrosion of the metallic portions of the e-vaping device to occur. Specifically, metal ions such as, for example, copper ions $Cu^{2+}$ or Iron ions $Fe^{2+}$ or $Fe^{3+}$, may dissolve in the pre-vapor solution as a result of the corrosion reaction, and may react with ingredients of the pre-vapor formulation, thereby decreasing the stability of the pre-vapor formulation. In addition, the metallic portions of the e-vaping device may undergo structural damage due to the dissolution of metal ions thereof, and may have cause the pre-vapor formulation to leak out of the e-vaping device over a period of time.

With respect to the actual corrosion process of the metallic portions of the e-vaping device, an oxidation of metal(s) forming portions of the e-vaping device, such as the cartridge or the reservoir, takes place when an oxygen gradient appears between the surface of the metallic portions of the e-vaping device and the pre-vaporization formulation, thus producing localized anode/cathode systems. The localized anode/cathode systems create an oxidation/reaction cycle where the metal(s) are oxidized to produce metal cations that dissolve into the pre-vaporization formulation and may react with ingredients of the pre-vaporization formulation to decrease the stability thereof.

SUMMARY OF THE INVENTION

At least one example embodiment relates to applying a coating to a metallic portion of an e-vaping device, the coating being configured to reduce or substantially prevent corrosion or oxidation of metal(s) of the metallic portion via a reaction with the pre-vaporization formulation.

Some example embodiments relate to a method of protecting a surface of an e-vaping device portion from corrosion, the method including preparing a coating mixture configured to protect the surface from corrosion, and coating the surface with a protective coating based on the coating mixture. The coating may be performed via one of electrodeposition, dipping, spraying, and vapor deposition, and the coating mixture may include a silane and/or a resin.

Some example embodiments relate to methods of depositing a protective coating on inside surfaces of metallic portions of an e-vaping device, such as inside surfaces of the heater or interior walls of the reservoir or cartridge, in order to protect the metallic portions from damage due to corrosion caused by a reaction between ingredients of the pre-vaporization formulation and the metals of the metallic portions. The protective coating deposition may be performed via, for example, electro-deposition or electro-spraying. The protective coating may also include hydrophobic graphene oxide polymer composites on, for example, copper or copper alloys.

In some example embodiments, surfaces of metallic portions of the e-vaping device that are typically in contact with the pre-vapor formulation may be treated in order to be substantially protected from corrosion. For example, during the manufacturing process of a metallic portion of the e-vaping device, a coating may be deposited on a surface of the metallic portion via electrodeposition, electro-less deposition or dipping. The coating may be formed of or include a mixture of silanes and resins, for example epoxy-resin-esters modified bis-[tri-ethoxy-silyl] ethane on steel. In example embodiments, hydrophobic graphene oxide-polymer composites can be deposited as a coating on a metallic portion, for example a copper portion of an e-vaping device, in order to reduce or substantially prevent oxidation and/or corrosion of the copper portion.

In example embodiments, the coating or coatings deposited on the metallic portions of the e-vaping device may be substantially non-porous, and may hinder or substantially prohibit contact between the surface of the metallic portion and the pre-vapor formulation. For example, a silane or graphene oxide coating combined with polymeric binders may withstand a typical operating temperature of the e-vaping device without degrading. For example, the deposited coating may be hydrophobic to further reduce or substantially prevent wetting and thus oxidation or corrosion of the metallic portions of the e-vaping device.

In some example embodiments, metallic parts or portions of the e-vaping device that are typically in contact with the pre-vapor formulation may be separately treated, e.g., may be electroplated with a protective coating prior to being assembled as the e-vaping device. For example, the metallic surfaces may be electroplated with a thin non-porous organic coating that is conformable and that is configured to withstand the operating temperatures of the heater in the e-vaping device. Alternatively, various metallic portions may be electroplated, or otherwise have a coating deposited thereon, after assembly of at least a part of the e-vaping device.

In some example embodiments, electrospray may also be used to deposit a coating on metallic portions of the e-vaping device. For example, thin or ultra-thin parylene coatings may be deposited over surfaces of the metallic portions of the e-vaping device that are typically in contact with the pre-vapor formulation. For example, the ultra-thin parylene coating may be applied under vacuum using either a spray method or a tumbler method to increase the temperature resistance of the coating as well as to decrease interaction with chemicals such as the ingredients of the pre-vapor formulation and/or UV light.

Example embodiments relate to an e-vaping device having improved corrosion resistance of the metallic parts thereof, an improved shelf life, and a decreased or substantially prevented metal dissolution or catalytic reaction on the surface(s) of metallic portions of the e-vaping device.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted to limit the intended scope of the claims. The accompanying drawings are not to be considered as drawn to scale unless explicitly noted.

FIG. 3 is a longitudinal cross-sectional view of another example embodiment of an e-vaping device;

FIG. 4 is a longitudinal cross-sectional view of another example embodiment of an e-vaping device.

DETAILED DESCRIPTION

Figure 1:
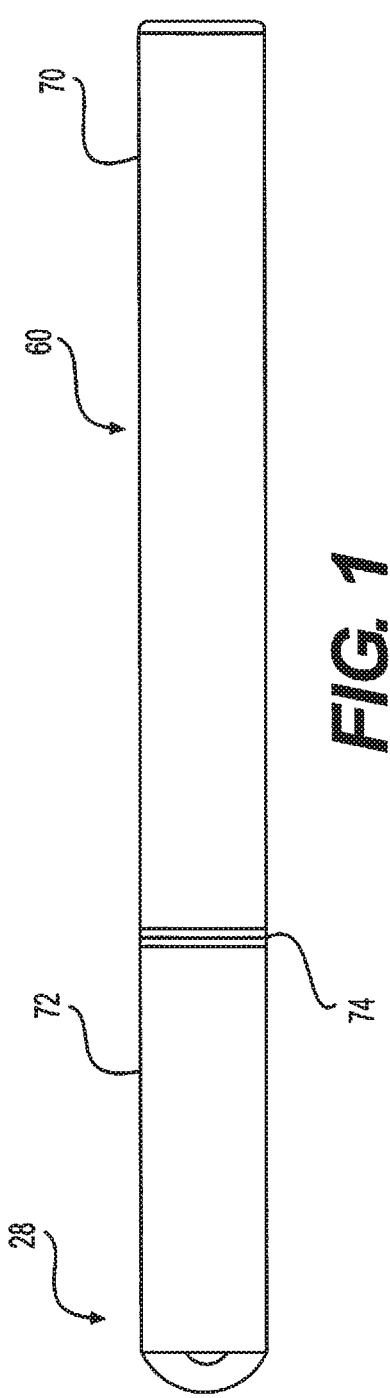
FIG. 1 is a side view of an e-vaping device, according to an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms "first," "second," "third," etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations and/or elements, but do not preclude the presence or addition of one or more other features, integers, steps, operations, elements and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

When the terms "about" or "substantially" are used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%.

As used herein, the term "vapor former" describes any suitable known compound or mixture of compounds that, in use, facilitates formation of a vapor and that is substantially resistant to thermal degradation at the operating temperature of the e-vaping device. Suitable vapor-formers consist of various compositions of polyhydric alcohols such as propylene glycol and/or glycerol or glycerin. In at least one embodiment, the vapor former is propylene glycol.

FIG. 1 is a side view of an e-vaping device 60, according to an example embodiment. In FIG. 1, the e-vaping device 60 includes a first section or cartridge 70 and a second section 72 or power supply section 72, which are coupled together at a threaded joint 74 or by other connecting structure such as a snug-fit, snap-fit, detent, clamp and/or clasp or the like. In at least one example embodiment, the first section or cartridge 70 may be a replaceable cartridge, and the second section 72 may be a reusable section. Alternatively, the first section or cartridge 70 and the second section 72 may be integrally formed in one piece. In at least one embodiment, the second section 72 includes a LED at a distal end 28 thereof. In example embodiments, the first section may be or include a tank 70 configured to hold the pre-vapor formulation and to be manually refillable.

Figure 2:
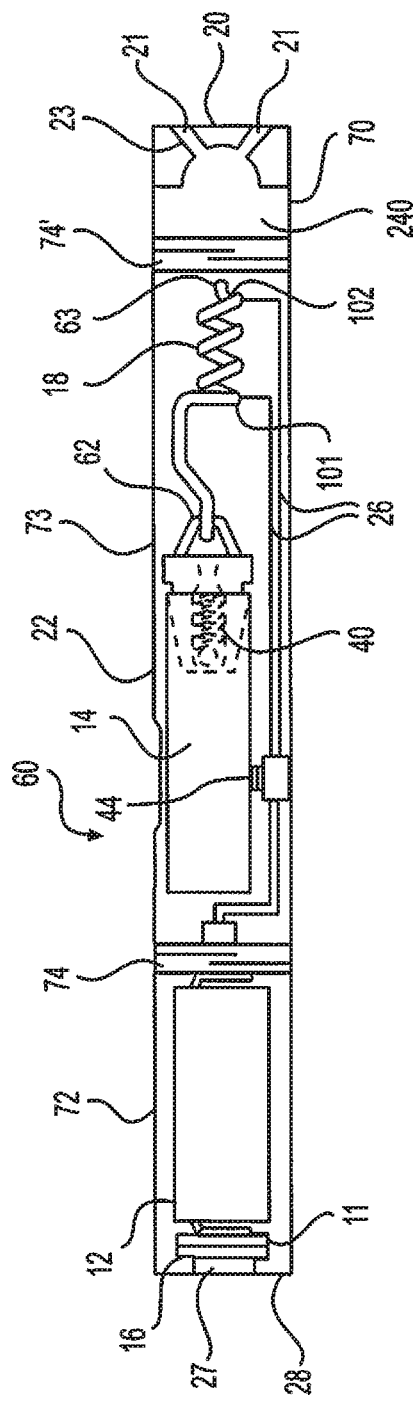
FIG. 2 is a longitudinal cross-sectional view of an e-vaping device, according to an example embodiment.

FIG. 2 is a cross-sectional view of an example embodiment of an e-vaping device. As shown in FIG. 2, the first section or cartridge 70 can house a mouth-end insert 20, a capillary tube 18, and a reservoir 14.

In example embodiments, the reservoir 14 may include a wrapping of gauze about an inner tube (not shown). For example, the reservoir 14 may be formed of or include an outer wrapping of gauze surrounding an inner wrapping of gauze. In at least one example embodiment, the reservoir 14 may be formed of or include an alumina ceramic in the form of loose particles, loose fibers, or woven or nonwoven fibers. Alternatively, the reservoir 14 may be formed of or include a cellulosic material such as cotton or gauze material, or a polymer material, such as polyethylene terephthalate, in the form of a bundle of loose fibers. A more detailed description of the reservoir 14 is provided below.

The second section 72 can house a power supply 12, control circuitry 11 configured to control the power supply 12, and a puff sensor 16. The puff sensor 16 is configured to sense when an operator of the e-vaping device is drawing on the e-vaping device 60, which triggers operation of the power supply 12 via the control circuitry 11 to heat the pre-vapor formulation housed in the reservoir 14, and thereby form a vapor. A threaded portion 74 of the second section 72 can be connected to a battery charger, when not connected to the first section or cartridge 70, to charge the battery or power supply section 12.

In example embodiments, the capillary tube 18 is formed of or includes a conductive material, and thus may be configured to be its own heater by passing current through the tube 18. The capillary tube 18 may be any electrically conductive material capable of being heated, for example resistively heated, while retaining the necessary structural integrity at the operating temperatures experienced by the capillary tube 18, and which is non-reactive with the pre-vapor formulation. Suitable materials for forming the capillary tube 18 are one or more of stainless steel, copper, copper alloys, porous ceramic materials coated with film resistive material, nickel-chromium alloys, and combinations thereof. For example, the capillary tube 18 is a stainless steel capillary tube 18 and serves as a heater via electrical leads 26 attached thereto for passage of direct or alternating current along a length of the capillary tube 18. Thus, the stainless steel capillary tube 18 is heated by, for example, resistance heating. Alternatively, the capillary tube 18 may be a non-metallic tube such as, for example, a glass tube. In such an embodiment, the capillary tube 18 also includes a conductive material such as, for example, stainless steel, nichrome or platinum wire, arranged along the glass tube and capable of being heated, for example resistively. When the conductive material arranged along the glass tube is heated, pre-vapor formulation present in the capillary tube 18 is heated to a temperature sufficient to at least partially volatilize pre-vapor formulation in the capillary tube 18.

In at least one embodiment, the electrical leads 26 are bonded to the metallic portion of the capillary tube 18. In at least one embodiment, one electrical lead 26 is coupled to a first, upstream portion 101 of the capillary tube 18 and a second electrical lead 26 is coupled to a downstream, end portion 102 of the capillary tube 18.

In operation, when an operator of the e-vaping device draws on the e-vaping device, the puff sensor 16 detects a pressure gradient caused by the drawing of the operator of the e-vaping device, and the control circuitry 11 controls heating of the pre-vapor formulation located in the reservoir 14 by providing power to the capillary tube 18. Once the capillary tube 18 is heated, the pre-vapor formulation contained within a heated portion of the capillary tube 18 is volatilized and emitted from the outlet 63, where the pre-vapor formulation expands and mixes with air and forms a vapor in mixing chamber 240.

As shown in FIG. 2, the reservoir 14 includes a valve 40 configured to maintain the pre-vapor formulation within the reservoir 14 and to open when the reservoir 14 is squeezed and pressure is applied thereto, the pressure being created when an operator of the e-vaping device draws on the e-vaping device at the mouth-end insert 20, which results in the reservoir 14 forcing the pre-vapor formulation through the outlet 62 of the reservoir 14 to the capillary tube 18. In at least one embodiment, the valve 40 opens when a critical, minimum pressure is reached so as to avoid inadvertently dispensing pre-vapor formulation from the reservoir 14. In at least one embodiment, the pressure required to press the pressure switch 44 is high enough such that accidental heating due to the pressure switch 44 being inadvertently pressed by outside factors such as physical movement or collision with outside objects is avoided.

The power supply 12 of example embodiments can include a battery arranged in the second section 72 of the e-vaping device 60. The power supply 12 is configured to apply a voltage to volatilize the pre-vapor formulation housed in the reservoir 14.

In at least one embodiment, the electrical connection between the capillary tube 18 and the electrical leads 26 is substantially conductive and temperature resistant while the capillary tube 18 is substantially resistive so that heat generation occurs primarily along the capillary tube 18 and not at the contacts.

The power supply section or battery 12 may be rechargeable and include circuitry allowing the battery to be chargeable by an external charging device. In example embodiments, the circuitry, when charged, provides power for a given number of draws through outlets of the e-vaping device, after which the circuitry may have to be re-connected to an external charging device.

In at least one embodiment, the e-vaping device 60 may include control circuitry 11 which can be, for example, on a printed circuit board. The control circuitry 11 may also include a heater activation light 27 that is configured to glow when the device is activated. In at least one embodiment, the heater activation light 27 comprises at least one LED and is at a distal end 28 of the e-vaping device 60 so that the heater activation light 27 illuminates a cap which takes on the appearance of a burning coal when the operator of the e-vaping device draws on the e-vaping device. Moreover, the heater activation light 27 can be configured to be visible to the operator of the e-vaping device. The light 27 may also be configured such that the operator of the e-vaping device can activate and/or deactivate the light 27 when desired, such that the light 27 is not activated during vaping if desired.

In at least one embodiment, the e-vaping device 60 further includes a mouth-end insert 20 having at least two off-axis, diverging outlets 21 that are uniformly distributed around the mouth-end insert 20 so as to substantially uniformly distribute vapor in the mouth of an operator of the e-vaping device during operation of the e-vaping device. In at least one embodiment, the mouth-end insert 20 includes at least two diverging outlets 21 (e.g., 3 to 8 outlets or more). In at least one embodiment, the outlets 21 of the mouth-end insert 20 are located at ends of off-axis passages 23 and are angled outwardly in relation to the longitudinal direction of the e-vaping device 60 (e.g., divergently). As used herein, the term "off-axis" denotes an angle to the longitudinal direction of the e-vaping device.

In at least one embodiment, the e-vaping device 60 is about the same size as a tobacco-based product. In some embodiments, the e-vaping device 60 may be about 80 mm to about 110 mm long, for example about 80 mm to about 100 mm long and about 7 mm to about 10 mm in diameter.

The outer cylindrical housing 22 of the e-vaping device 60 may be formed of or include any suitable material or combination of materials. In at least one embodiment, the outer cylindrical housing 22 is formed at least partially of metal and is part of the electrical circuit connecting the control circuitry 11, the power supply 12 and the puff sensor 16.

As shown in FIG. 2, the e-vaping device 60 can also include a middle section (third section) 73, which can house the pre-vapor formulation reservoir 14 and the capillary tube 18. The middle section 73 can be configured to be fitted with a threaded joint 74' at an upstream end of the first section or cartridge 70 and a threaded joint 74 at a downstream end of the second section 72. In this example embodiment, the first section or cartridge 70 houses the mouth-end insert 20, while the second section 72 houses the power supply 12 and the control circuitry 11 that is configured to control the power supply 12.

FIG. 3 is a cross-sectional view of an e-vaping device according to an example embodiment. In at least one embodiment, the first section or cartridge 70 is replaceable so as to avoid the need for cleaning the capillary tube 18. In at least one embodiment, the first section or cartridge 70 and the second section 72 may be integrally formed without threaded connections to form a disposable e-vaping device.

As shown in FIG. 3, in other example embodiments, a valve 40 can be a two-way valve, and the reservoir 14 can be pressurized. For example, the reservoir 14 can be pressurized using a pressurization arrangement 405 configured to apply constant pressure to the reservoir 14. As such, emission of vapor formed via heating of the pre-vapor formulation housed in the reservoir 14 is facilitated. Once pressure upon the reservoir 14 is relieved, the valve 40 closes and the heated capillary tube 18 discharges any pre-vapor formulation remaining downstream of the valve 40.

FIG. 4 is a longitudinal cross-sectional view of another example embodiment of an e-vaping device. In FIG. 4, the e-vaping device 60 can include a central air passage 24 in an upstream seal 15. The central air passage 24 opens to the inner tube 65. Moreover, the e-vaping device 60 includes a reservoir 14 configured to store the pre-vapor formulation. The reservoir 14 includes the pre-vapor formulation and optionally a storage medium 25 such as gauze configured to store the pre-vapor formulation therein. In an embodiment, the reservoir 14 is contained in an outer annulus between the outer tube 6 and the inner tube 65. The annulus is sealed at an upstream end by the seal 15 and by a stopper 10 at a downstream end so as to prevent leakage of the pre-vapor formulation from the reservoir 14. The heater 19 at least partially surrounds a central portion of a wick 220 such that when the heater is activated, the pre-vapor formulation present in the central portion of the wick 220 is vaporized to form a vapor. The heater 19 is connected to the battery 12 by two spaced apart electrical leads 26. The e-vaping device 60 further includes a mouth-end insert 20 having at least two outlets 21. The mouth-end insert 20 is in fluid communication with the central air passage 24 via the interior of inner tube 65 and a central passage 64, which extends through the stopper 10.

The e-vaping device 60 may include an air flow diverter comprising an impervious plug 30 at a downstream end 82 of the central air passage 24 in seal 15. In at least one example embodiment, the central air passage 24 is an axially extending central passage in seal 15, which seals the upstream end of the annulus between the outer and inner tubes 6, 65. The radial air channel 32 directing air from the central passage 20 outward toward the inner tube 65. In operation, when an operator of the e-vaping device draws on the e-vaping device, the puff sensor 16 detects a pressure gradient caused by the drawing of the operator of the e-vaping device, and as a result the control circuitry 11 controls heating of the pre-vapor formulation located in the reservoir 14 by providing power the heater 19.

Figure 5A:
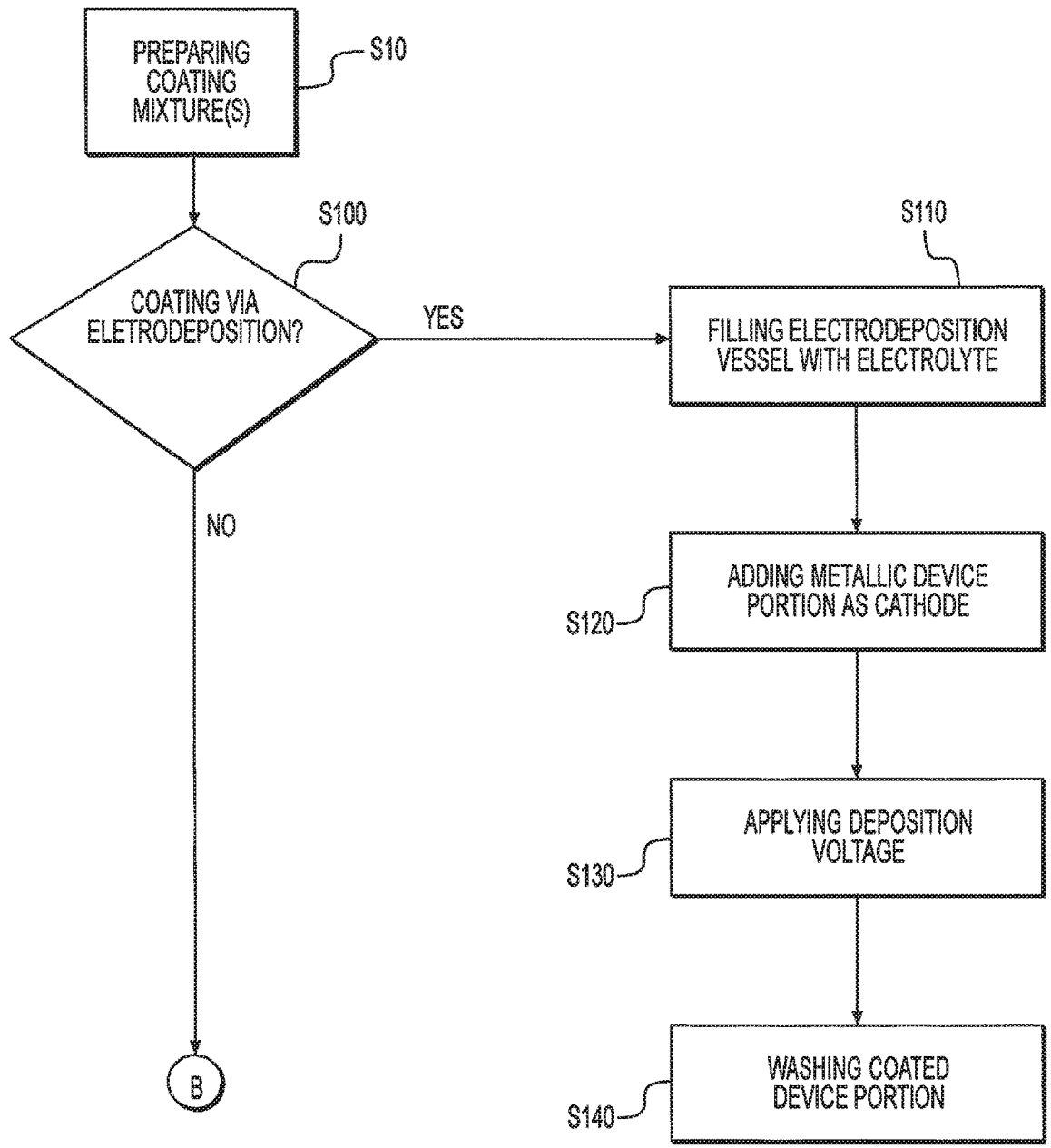
FIGS. 5A-5D are flow charts illustrating a method of depositing a protective coating on inside surfaces of metallic portions of an e-vaping device, according to at least one example embodiment.
Figure 5B:
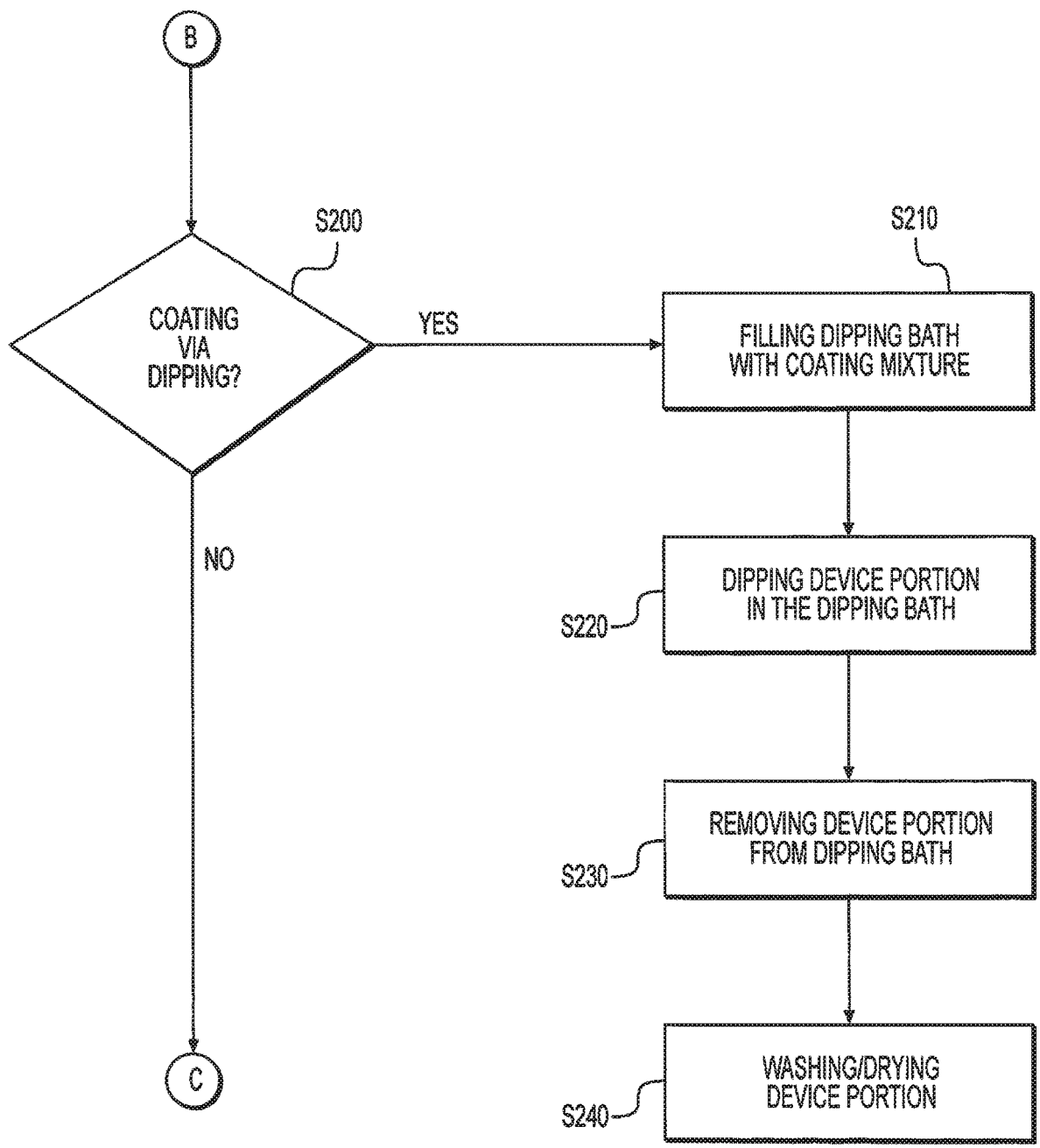
Figure 5C:
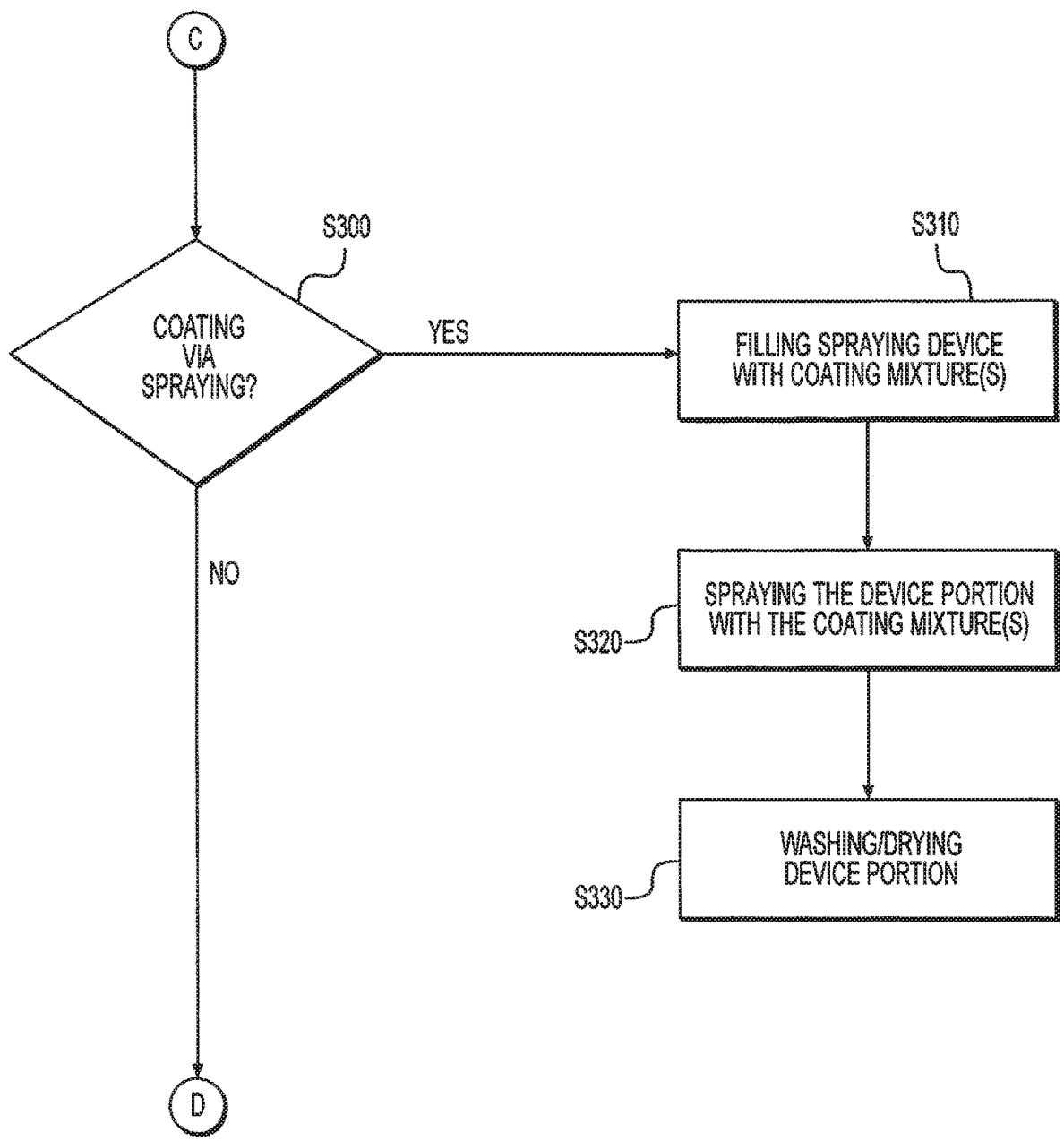
Figure 5D:
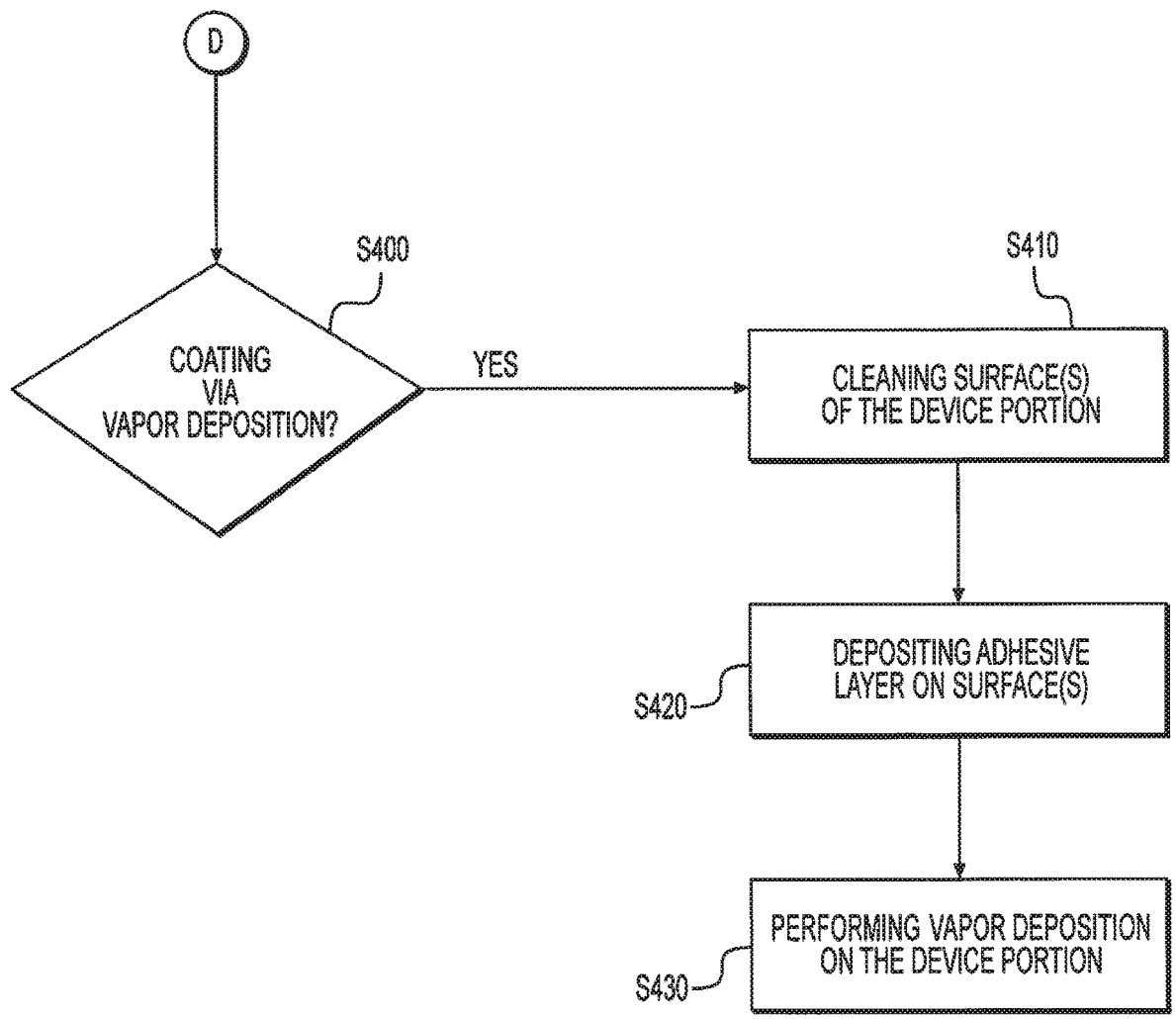

FIGS. 5A-5D are flow charts illustrating a method of depositing a protective coating on inside surfaces of metallic portions of an e-vaping device, according to at least one example embodiment. In FIG. 5A, the method starts at S10 and preparing a coating mixture configured to protect the surface from corrosion. In some example embodiments, preparing the coating mixture includes preparing a first mixture by dissolving a first polymer, preparing a second mixture by dissolving a second polymer, and preparing a third mixture by dissolving a silane.

In some example embodiments, preparing the first mixture includes dissolving a polymer at a concentration of about 1 to about 5% by weight in water, adding acetic acid to adjust a pH of the first mixture to be smaller than or equal to 6, and heating the first mixture to between about 50° C. and about 70° C., followed by cooling at room temperature. In some example embodiments, the method further includes adding a filler at a weight ratio of about 10 parts of polymer to 1 part of filler. In some example embodiments, fillers may include silica in a colloidal dispersion such as, for example, a commercially available dispersion that is stable at low pH. The silica dispersion may be from about 0.1% to about 30% by weight of the treatment solution on a dry weight basis, and for example may be below 20%. A colloidal silica dispersion may be a dispersion of discrete silica particles in the range of 1 nm to 100 nm. In addition, the filler may contain solid particles of graphene oxide, $TiO_2$, clay, $ZrO_2$, and the like at concentrations of 0.1% to 30%, for example below 20%.

In some example embodiments, the polymer is or includes chitosan and/or the pH is in the range of about 4 to about 5.

In some example embodiments the filler is added at a weight ratio of about 100 parts of polymer to 1 part of filler.

In some example embodiments, preparing the second mixture includes dissolving a cationic polymer in a water dispersion that includes about 30% to about 40% of particulate dispersion. The particulate dispersion may include at least one of solid polymer particles, graphene oxide particles and colloidal silica particles. A filler may be added at a weight ratio of about 10 parts of polymer to 1 part of filler, or at a weight ratio of about 100 parts of polymer to 1 part of filler.

In some example embodiments, preparing the third mixture includes mixing a solvent with a silane at about 5% to about 20% by weight of the silane, adding acetic acid to adjust the pH to stabilize hydrolyzed silane, and mixing the third mixture via agitation at room temperature for about 10 min to about 1 hour. The solvent may include water, or alternatively methanol. The silane may include at least one of tetraethyl orthosilicate (TEOS) and 1,2-Bis(triethoxysilyl)ethane (BTSE).

In some example embodiments, preparing the coating mixture includes combining the first mixture and the third mixture at a ratio of about 6 to 1, combining the first mixture and the third mixture at a ratio of about 6 to 1 without the step of adding the filler, combining the second mixture and the third mixture at a ratio of about 6 to 1, or combining the second mixture and the third mixture at a ratio of about 6 to 1 without the step of adding the filler.

In example embodiments, the coating mixture includes several parts. For example, the coating mixture includes up to five (5) different parts. The coating mixture includes a first part that includes water and/or methanol. A second part includes an organic acid to control pH such as, for example, acetic acid. The acid(s) present in the pre-vapor formulation may have a boiling point of at least about 100° C. For example, the acid(s) may have a boiling point ranging from about 100° C. to about 300° C., or about 150° C. to about 250° C. (e.g., about 160° C. to about 240° C., about 170° C. to about 230° C., about 180° C. to about 220° C. or about 190° C. to about 210° C.). According to at least one example embodiment, the acid(s) present in the coating may include one or more of pyruvic acid, formic acid, oxalic acid, glycolic acid, acetic acid, isovaleric acid, valeric acid, propionic acid, octanoic acid, lactic acid, levulinic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-pentenoic acid, phenylacetic acid, 3-phenylpropionic acid, hydrochloric acid, phosphoric acid, sulfuric acid, and combinations thereof.

In example embodiments, the coating mixture includes a third part that includes an organic polymer. For example, the third part includes a linear polysaccharide such as chitosan, or other organic polymer that includes multiple reactive sites such as hydroxyl and amine groups for crosslinking or hydrogen bonding with the other ingredients of the coating mixture. The organic polymer may be in solution, or may be in the form of an aqueous cationic dispersion. Other organic polymers, such as epoxies, polyurethanes, polyesters, polyacrylates, and the like, can also be used as cationic water dispersions in the coating. In example embodiments, a natural polymer like chitosan, a modified starch or natural gum or another biopolymer are advantageous because they are biocompatible and non-toxic. The polymer concentration expressed in total solids in the coating may range from about 0.5% to about 40% by weight of the coating solution.

In example embodiments, the coating mixture includes a fourth part that includes a filler such as, for example, silica in a colloidal dispersion. For example, the silica may be or include a commercially available dispersion of silica that is stable at low pH at a concentration of about 0.1% to about 30% by weight of the coating solution on a dry weight basis. For example, the concentration of silica may be smaller to or equal to about 20%. The fourth part may include a colloidal silica dispersion, which is a dispersion of discrete silica particles, in the range of about 1 nm to about 100 nm. In example embodiments, the fourth part may include solid graphene oxide, $TiO_2$, clay, $ZrO_2$, $ZrO_2$—$Y_2O_3$, $CeO_2$, $Al_2O_3$, and the like, at a concentration of about 0.1% to about 30%, and for example at a concentration of smaller than or equal to about 20%.

In example embodiments, the coating mixture includes a fifth part that includes a water soluble silane. For example, multiple silanes may be used in the coating, such as Tetraethyl orthosilicate (TEOS), Tetramethyl orthosilicate (TMOS), 3-(2-Aminoethylamino)propyldimethoxymethylsilane (AEAPS), (3-Glycidoxypropyl)methyldiethoxysilane (GPTMS), (3-Aminopropyl)triethoxysilane (APTES), bis-1, 2-(triethoxysilyl) ethane (BTSE) and Poly(methyl methacrylate) (PMMA), which typically provide desired reactivities and expected compatibility with the other components of the coating. For example, the silane concentration may be between about 0.1% and about 1% by weight of the coating.

In example embodiments, a method of forming a protective coating on a surface of a portion of an e-vaping device may include preparing several mixtures. For example, example embodiments of the method include preparing three (3) mixtures, A, B and C.

Mixture A may be prepared by dissolving an organic polymer (such as, for example, chitosan) at concentration of about 1% to about 5% by weight in a solvent (such as water or methanol). An organic acid such as, for example, acetic acid may be used to adjust the pH to be below about 6, and for example in the range of about 4 to 5. The method may further include heating the mixture to between about 50° C. and about 70° C. in order to facilitate dissolution, followed by cooling of the mixture to room temperature. Optionally, a filler may be added at a weight ratio of organic polymer (dry basis) to filler of about 10 (10 parts of polymer to 1 part of filler). For some fillers, the ratio may be reduced to about 100/1 to create a workable viscosity.

Mixture B may be prepared by preparing a cationic polymer water dispersion with solids of about 30% to about 40%. Optionally, a filler may be added at a weight ratio of organic polymer (dry basis) to filler of about 10 (10 parts of polymer to 1 part of filler). For some fillers, the ratio may be reduced to about 100/1 to create a workable viscosity.

Mixture C may be prepared by preparing a solvent solution (water or methanol) including a functional or non-functional silane such as, for example, TEOS or BTSE. Acetic acid may be added to adjust the pH to a range that promotes the stability of the hydrolyzed silane. The mixture may also include up to between about 5% and about 20% by weight of the silane and be mixed by agitation at room temperature for between about 10 min to about 1 hr.

Example embodiments of the method of forming a protective coating on a surface of a portion of an e-vaping device include one or more treatments using the above mixtures to form the coating. For example, a first treatment may include combining Mixture A with Mixture C described above at a weight ratio of C:A of about 6:1. An example second treatment may include combining Mixture A without the filler with Mixture C at a weight ratio of A:C of about 6:1. An example third treatment may include combining Mixtures B and C at a weight ratio of B:C of about 6:1. An example fourth treatment may include combining Mixture B without the filler and Mixture C at a weight ratio of B:C of about 6:1.

In some example embodiments, the method continues to S100 where, if the coating is performed via electrodeposition, the method at S110 includes filling an electrodeposition vessel or bath with the coating mixture, the electrodeposition vessel including an anode and a cathode. At S120, the cathode is or includes the metallic e-vaping device portion. At S130, the method includes applying a deposition voltage to the anode and the cathode to deposit the coating film on the surface of the e-vaping device portion. In some example embodiments, depositing the coating film includes applying an electrodeposition voltage between the anode and the cathode, the voltage being between about 1 V to about 50 V, for a duration ranging from a few seconds to 10 minutes, for example between 2 and 5 minutes. In some example embodiments, depositing the coating film includes applying an electrodeposition current between the anode and the cathode that is less than about 3 A, or for example between about 5 mA and about 200 mA. A resulting thickness of the coating may be between less than one micrometer (μm) and tens of micrometers.

In some example embodiments, the method further includes at S140 removing the e-vaping device portion from the electrodeposition bath, washing the e-vaping device portion with a solvent or water, and drying the e-vaping device portion. For example, the drying may be performed at a temperature between about 50° C. to about 200° C. for a period of time between about 1 mn to about 30 mn.

In some example embodiments, when the coating is performed via dipping at S200, the method includes filling a dipping bath with the coating mixture at S210, dipping the e-vaping device portion in the dipping bath at S220, removing the e-vaping device portion from the dipping bath at S230, and washing the e-vaping device portion of any residue and drying the e-vaping device portion at S240.

In some example embodiments, when the coating is performed via spraying at S300, the coating includes filling a spraying device with the coating mixture at S310, spraying the e-vaping device portion with the coating mixture and S320, and washing the e-vaping device portion of any residue and drying the e-vaping device portion at S330.

In some example embodiments, when the coating is performed via vapor deposition at S400, the coating includes cleaning the surface of the e-vaping device portion at S410, depositing an intermediate adhesive layer on the surface of the e-vaping device portion at S420. Depositing the intermediate adhesive layer includes dipping the e-vaping device portion in a solution including about 0.05% to about 5% by volume of a silane solution. The silane solution includes about 50% water and about 50% isoproponal mixture, or about 2% to about 10% methanol based BTSE. The intermediate adhesive layer may include silane, carboxylic acid, or an anhydride group containing one or more polymers. The method may also include performing vapor deposition to deposit a coat on the surface of the e-vaping device portion at S430. The coat may include parylene, and performing the vapor deposition, which may be one of chemical vapor deposition and physical vapor deposition, includes heating parylene at a temperature of equal to or greater than about 600° C. to pyrolize parylene dimer into a monomer, and depositing the parylene monomer over metallic portions of the e-vaping device portion at room temperature. For example, the thickness of the intermediate adhesive layer may be between about 0.1 μm and about 5 μm, and the thickness of the parylene may be between about 0.05 μm and about 2 μm. The method may also include cleaning via vapor degreasing, ultrasound cleaning, and/or machine washing the e-vaping device portion, as well as drying the e-vaping device portion at S440.

Example embodiments having thus been described, it will be obvious that the same may be varied in many ways. Such variations are not to be regarded as a departure from the intended spirit and scope of example embodiments, and all modifications as would be obvious to one skilled in the art are intended to be included within the scope of the following claims.

What is claimed is:

1. A method of protecting an inside surface of an e-vaping device portion from corrosion, the method comprising:
preparing a coating mixture configured to protect the inside surface from corrosion and a pre-vapor formulation, the coating mixture configured to withstand a repeatable operating temperature cycle of the e-vaping device without degrading, and including preparing a first mixture by dissolving a first polymer and preparing a second mixture by dissolving a second polymer, preparing the second mixture includes dissolving the second polymer in a water dispersion that includes about 30% to about 40% of particulate dispersion, the second polymer being a cationic polymer and the particulate dispersion includes solid polymer particles; and
coating the inside surface with a permanent protective coating based on the coating mixture;
the coating being performed via electrodeposition, vapor deposition, or both; and
the coating mixture including a silane, a resin, or both.

2. The method of claim 1, wherein the preparing the coating mixture comprises:
preparing a third mixture by dissolving a silane.

3. The method of claim 2, wherein the preparing the first mixture comprises:
dissolving the first polymer at a concentration of about 1% to about 5% by weight in water;
adding acetic acid to adjust a pH of the first mixture to be smaller than or equal to 6; and heating the first mixture to between about 50° C. and about 70° C.

4. The method of claim 3, further comprising:
adding a filler at a weight ratio of about 10 parts of the first polymer to 1 part of filler.

5. The method of claim 4, wherein the pH of the first mixture is in the range of about 4 to about 5.

6. The method of claim 4, wherein the adding the filler comprises adding the filler at a weight ratio of about 100 parts of the first polymer to 1 part of filler.

7. The method of claim 3, wherein the first polymer comprises chitosan.

8. The method of claim 2, wherein the preparing the third mixture comprises:
mixing a solvent with the silane at about 5% to about 20% by weight of the silane;
adding acetic acid to adjust the pH to stabilize hydrolyzed silane; and
mixing the third mixture via agitation at room temperature for about 10 mn to about 1 hour.

9. The method of claim 8, wherein the solvent comprises water, methanol, or both.

10. The method of claim 8, wherein the silane comprises TEOS, BTSE, or both.

11. The method of claim 2, wherein when the coating is performed via vapor deposition, the coating comprises:
cleaning the inside surface of the e-vaping device portion;
depositing an intermediate adhesive layer on the inside surface of the e-vaping device portion; and
performing vapor deposition to deposit a coat on the inside surface of the e-vaping device portion.

12. The method of claim 11, wherein the cleaning comprises:
one of vapor degreasing, ultrasound cleaning, machine washing, a sub-combination thereof, or a combination thereof, the e-vaping device portion; and
drying the e-vaping device portion.

13. The method of claim 11, wherein the depositing comprises dipping the e-vaping device portion in a solution including about 0.05% to about 5% by volume of a silane solution.

14. The method of claim 13, wherein the silane solution comprises one of:
about 50% water and about 50% isopropanol mixture; or
about 2% to about 10% methanol based BTSE.

15. The method of claim 11, wherein the intermediate adhesive layer comprises one of silane, carboxylic acid, an anhydride group containing one or more polymers, a sub-combination thereof, or a combination thereof.

16. The method of claim 11, wherein the coat comprises parylene.

17. The method of claim 16, wherein the performing the vapor deposition comprises:
heating parylene at a temperature of equal to or greater than about 600° C. to pyrolize a parylene dimer into a monomer; and
depositing the parylene monomer over metallic portions of the e-vaping device portion at room temperature.

18. The method of claim 17, wherein a thickness of the parylene is between about 0.05 μm and about 2 μm.

19. The method of claim 16, wherein the performing the vapor deposition comprises performing one of chemical vapor deposition or physical vapor deposition.

20. The method of claim 11, wherein a thickness of the intermediate adhesive layer is between about 0.1 μm and about 5 μm.

21. The method of claim 1, further comprising:
adding a filler at a weight ratio of about 10 parts of the second polymer to 1 part of filler.

22. The method of claim 21, wherein the adding the filler comprises adding the filler at a weight ratio of about 100 parts of the second polymer to 1 part of filler.

23. The method of claim 1, wherein the preparing the coating mixture comprises:
combining the second mixture and the third mixture at a ratio of about 6 to 1.

24. The method of claim 1, wherein the preparing the coating mixture comprises:
combining the second mixture and the third mixture at a ratio of about 6 to 1.

25. The method of claim 1, wherein when the coating is performed via electrodeposition, the coating the inside surface comprises:
filling an electrodeposition vessel with the coating mixture, the electrodeposition vessel including an anode and a cathode;
connecting the cathode with the e-vaping device portion; and
depositing the coating mixture on the inside surface of the e-vaping device portion.

26. The method of claim 25, wherein the depositing the coating mixture comprises:
applying an electrodeposition voltage between the anode and the cathode of between about 1 V to about 50 V.

27. The method of claim 25, wherein the depositing the coating mixture comprises:
applying an electrodeposition current between the anode and the cathode that is less than about 3 A.

28. The method of claim 27, wherein the electrodeposition current is between about 5 mA and about 200 mA.

29. The method of claim 25, further comprising:
removing the e-vaping device portion from the electrodeposition vessel;
washing the e-vaping device portion; and
drying the e-vaping device portion.

30. The method of claim 29, wherein the drying the e-vaping device portion is performed at a temperature between about 50° C. to about 200° C. for a period of time between about 1 mn to about 30 mn.

31. The method of claim 1, wherein the inner surfaces of the e-vaping device include inside surfaces of a heater, interior walls of a reservoir configured to store the pre-vapor formulation, or a combination thereof.

32. The method of claim 1, wherein the coating mixture further comprises a filler, wherein the filler includes at least one of $TiO_2$, clay, $ZrO_2$, $ZrO_2$-$Y_2O_3$, $CeO_2$, $Al_2O_3$, or a combination thereof.

* * * * *